United States Patent
Arnold et al.

(10) Patent No.: US 7,105,502 B2
(45) Date of Patent: Sep. 12, 2006

(54) NITRIC OXIDE-RELEASING IMIDATE AND THIOIMIDATE DIAZENIUMDIOLATES

(75) Inventors: Ernst V Arnold, Hagerstown, MD (US); Larry K Keefer, Bethesda, MD (US); Joseph A Hrabie, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 258 days.

(21) Appl. No.: 10/702,849

(22) Filed: Nov. 6, 2003

(65) Prior Publication Data

US 2004/0092484 A1    May 13, 2004

Related U.S. Application Data

(62) Division of application No. 09/950,162, filed on Sep. 10, 2001, now Pat. No. 6,673,338.

(51) Int. Cl.
*A61K 31/655* (2006.01)
*C07C 291/02* (2006.01)

(52) U.S. Cl. .................. 514/149; 514/647; 534/550; 534/566

(58) Field of Classification Search ................ 514/149, 514/647; 534/550, 566
See application file for complete search history.

(56) References Cited

U.S. PATENT DOCUMENTS

| 5,155,137 A | 10/1992 | Keefer et al. |
| 5,212,204 A | 5/1993 | Keefer et al. |
| 5,674,894 A | 10/1997 | Currie et al. |
| 5,770,645 A | 6/1998 | Stamler et al. |
| 6,232,336 B1 | 5/2001 | Hrabe et al. |

FOREIGN PATENT DOCUMENTS

| WO | WO 93/13055 A1 | 7/1993 |
| WO | WO 94/27957 A1 | 12/1994 |
| WO | WO 96/36639 A1 | 11/1996 |
| WO | WO 96/40665 A1 | 12/1996 |

OTHER PUBLICATIONS

Arnold et al., *Tetrahedron Letters*, 41, 8421-8424 (2000).
Arnold et al. *Am. Chem. Soc.*, $220^{th}$, *INOR-111*, Abstr. pap. (2000).
Severina et al., *Biochem. Mo. Bio. Int.*, 36 (4), 913-925 (1995).
Southan et al., *Nitric Oxide*, 2 (4), 270-286 (1998).
Soulere et al., *Bioorg. Med. Chem.* 10 (12), 1347-1350 (2000).
Boschi et al., *Bioorg. Med. Chem.*, 8(7), 1727-1732 (2000).
Freeman et al., *J. Org. Chem.*, 35(9), 3107-3110 (1970).
Volodarskii et al., *Chem. Abstr.* 85, No. 159592 (1976).
Hrabie et al., *Bioconjugate Chemistry*, 10, 838-842 (1999).

*Primary Examiner*—Kamal A. Saeed
(74) *Attorney, Agent, or Firm*—Leydig, Voit & Mayer, Ltd.

(57) ABSTRACT

The invention provides NO- or NO⁻-releasing imidate; and thioimidate, diazeniumdiolates, in which the $N_2O_2^-$ functional group is bonded to a carbon atom. The imidate and thioimidate diazeniumdiolates are bound to a polymer or a substrate.

18 Claims, No Drawings

NITRIC OXIDE-RELEASING IMIDATE AND THIOIMIDATE DIAZENIUMDIOLATES

CROSS-REFERENCE TO RELATED PATENT APPLICATIONS

This patent application is a divisional of U.S. patent application Ser. No. 09/950,162, filed Sep. 10, 2001, now U.S. Pat. No. 6,673,338.

FIELD OF THE INVENTION

This invention relates to nitric oxide-releasing imidate and thioimidate diazeniumdiolates, to compositions comprising such compounds, to methods of using such compounds and compositions, and to a method for the preparation of nitric oxide-releasing imidate and thioimidate diazeniumdiolates.

BACKGROUND OF THE INVENTION

Nitric oxide (NO) has been implicated as part of a cascade of interacting agents involved in a wide variety of bioregulatory processes, including the physiological control of blood pressure, macrophage-induced cytostasis and cytotoxicity, and neurotransmission (Moncada et al., "Nitric Oxide from L-Arginine: A Bioregulatory System," *Excerpta Medica*, International Congress Series 897, Elsevier Science Publishers B.V.: Amsterdam (1990); Marletta et al., *Biofactors* 2: 219–225 (1990); Ignarro, *Hypertension (Dallas)* 16: 477–483 (1990); Kerwin et al., *J. Med. Chem.* 38: 4343–4362 (1995); and Anggard, *Lancet* 343: 1199–1206 (1994)). Given that NO plays a role in such a wide variety of bioregulatory processes, great effort has been expended to develop compounds capable of releasing NO. Some of these compounds are capable of releasing NO spontaneously, e.g., by hydrolysis in aqueous media, whereas others are capable of releasing NO upon being metabolized (Lefer et al., *Drugs Future* 19: 665–672 (1994)).

Several types of compounds of the general structure

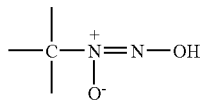

have been known for many years. Traube (*Liebigs Ann. Chem.* 300: 81–123 (1898)) reported the preparation of a number of such compounds and noted that treatment of the compounds with acid produced a "brown gas." Given that the brown gas is nitrogen dioxide which may be produced directly, the release of brown gas by the compounds prepared by Traube is not, in and of itself, evidence of NO release. Compounds of the structural type reported by Traube are known to require harsh treatment with mineral acids to release any gas and such treatment is, of course, incompatible with biological utility.

Another compound, which has the structure

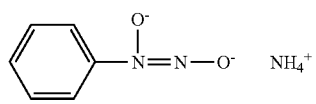

and which has been named cupferron, has been shown by Kubrina et al., (*Izvestia Akademii Nauk SSSR Seriia Biologicheskaia* 6: 844–850 (1988) English Trans.: Biol. Bull. Acad. Sci. USSR. 533–538, (1988)) to generate NO in vivo. In addition, the antibiotics alanosine ($C(O)(OH)CH(NH_2)CH_2N(O)=NOH$) and dopastin ($CH_3CH=CHC(O)NHCH_2CH(i\text{-propyl})\text{-}N(O)=NOH$), as well as cupferron, have been shown to release NO in vivo by enzymatic oxidation (Alston et al., *J. Biol. Chem.* 260: 4069–4074 (1985)).

Many of the known diazeniumdiolates and their clinical applications are disclosed in recently issued patents. For example, U.S. Pat. No. 4,954,526 (Keefer et al.) discloses nitric oxide-primary amine complexes useful as cardiovascular agents. U.S. Pat. No. 5,039,705 (Keefer et al.) and U.S. Pat. No. 5,208,233 (Keefer et al.) disclose anti-hypertensive compositions of secondary amine-nitric oxide adducts. U.S. Pat. No. 5,155,137 (Keefer et al.) and U.S. Pat. No. 5,250,550 (Keefer et al.) disclose complexes of nitric oxide with polyamines. U.S. Pat. No. 5,405,919 (Keefer et al.), U.S. Pat. No. 5,525,357 (Keefer et al.) and U.S. Pat. No. 5,718,892 (Keefer et al.) disclose polymer-bound nitric oxide/nucleophile adduct compositions. U.S. Pat. No. 5,366,997 (Keefer et al.) discloses oxygen-substituted derivatives of nucleophile-nitric oxide adducts as nitric oxide donor drugs. U.S. Pat. No. 5,389,675 (Christodoulou et al.) discloses mixed ligand complexes of nitric oxide-nucleophile adducts. U.S. Pat. No. 5,632,981 (Saavedra et al.) discloses biopolymer-bound nitric oxide-releasing compositions. U.S. Pat. No. 5,691,423 (Smith et al.) discloses polysaccharide-bound nitric oxide-nucleophile adducts. U.S. Pat. No. 5,721,365 (Keefer et al.) discloses N-substituted piperazine diazeniumdiolates. U.S. Pat. No. 5,185,376 (Diodati et al.) discloses therapeutic inhibition of platelet aggregation by nucleophile-nitric oxide complexes. U.S. Pat. No. 5,650,447 (Keefer et al.) discloses nitric oxide-releasing polymers to treat restenosis and related disorders. U.S. Pat. No. 5,676,963 (Keefer et al.) discloses implants, prostheses, and stents comprising polymer-bound nitric oxide/nucleophile adducts capable of releasing nitric oxide. U.S. Pat. No. 5,700,830 (Korthius et al.) discloses the use of nitric oxide adducts for reducing metastatic risk. U.S. Pat. No. 5,714,511 (Saavedra et al.) U.S. Pat. No. 5,814,666 (Keefer et al.) disclose selective prevention of organ injury in sepsis and shock using selective release of nitric oxide in vulnerable organs. U.S. Pat. No. 5,731,305 (Keefer et al.) discloses anti-hypertension compositions of secondary amine-nitric oxide adducts. U.S. Pat. No. 5,910,316 (Keefer et al.) discloses encapsulated and non-encapsulated nitric oxide generators useful as antimicrobial agents.

Other diazeniumdiolates useful in a host of applications include those described in U.S. patent application Ser. No. 09/254,301 (Saavedra et al.), which discloses $O^2$-arylated and $O^2$-glycosylated diazeniumdiolates, and U.S. Pat. No. 6,232,336 (Hrabie et al.), which discloses amidine- or enamine-derived diazeniumdiolates.

Despite the extensive literature available on NO and nitric oxide-releasing compounds, there remains a need for stable nitric oxide-releasing compounds in which the nitric oxide-releasing group $N_2O_2^-$ is bonded directly to a carbon atom and that serve as versatile intermediates in the preparation of a wide variety of therapeutic nitric oxide-releasing compounds.

BRIEF SUMMARY OF THE INVENTION

The invention described herein provides for a novel class of imidate and thioimidate diazeniumdiolates and their preparation. The imidate and thioimidate diazeniumdiolates are useful therapeutic compounds and serve as important building blocks in the synthesis of other biologically important NO-releasing compounds. These and other advantages of the present invention, as well as additional inventive features, will be apparent from the description of the invention provided below.

The invention provides NO- or NO⁻-releasing imidate or thioimidate diazeniumdiolates in which the $N_2O_2^-$ functional group is bonded to a carbon atom. The invention also provides compositions comprising such diazeniumdiolate compounds, and methods of using such compounds and compositions. The invention further provides a method for the preparation of NO- or NO⁻-releasing imidate or thioimidate diazeniumdiolates.

DETAILED DESCRIPTION OF THE INVENTION

The novel class of imidate and thioimidate diazeniumdiolates is capable of releasing nitric oxide under physiological conditions. These compounds are useful for treating biological conditions where a release of nitric oxide is beneficial.

The invention provides a novel class of NO-releasing imidate and thioimidate diazeniumdiolates of the formula:

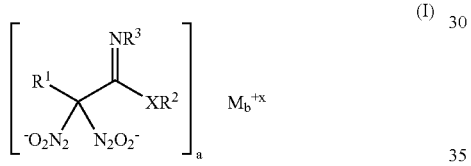

wherein X is O or S; $R^1$ is hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted alkoxy, nitrile, halo, an unsubstituted or substituted benzyl, an unsubstituted or substituted phenyl, an unsubstituted or substituted naphthyl, an unsubstituted or substituted piperazino, an unsubstituted or substituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, an unsubstituted or substituted tolyl, xylyl, anisyl, mesityl, an unsubstituted or substituted acetoxy, carboxy, an unsubstituted or substituted carboxyethyl, an unsubstituted or substituted alkylcarbonyl, thiol, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, an unsubstituted or substituted nitrophenyl, trialkylsilyl or nitro; $R^2$ is an unsubstituted or substituted $C_{1-12}$ straight chain alkyl or an unsubstituted,substituted $C_{3-12}$ branched chain alkyl, a phenyl, or naphthyl; $R^3$ is hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted $C_{3-8}$ cycloalkyl, a $C_{3-8}$ heterocyclic ring, an unsubstituted or substituted naphthyl, an unsubstituted or substituted tetrahydronaphthyl, an unsubstituted or substituted octahydronaphthyl, benzyl or substituted benzyl, or phenyl or substituted phenyl; and $M^{+x}$ is a pharmaceutically acceptable cation, x is the valence of the cation, and a and b are the smallest integers that result in a neutral compound. The substituent $R^1$ can be further substituted with at least one nitric oxide-releasing functional group.

Any one or more of $R^1$, $R^2$, and $R^3$ of formula (I) can be substituted. Generally each of $R^1$, $R^2$, and $R^3$ can have 1 to 3 substituents that are independently selected from the group consisting of alkyl, aryl, such as phenyl or naphthyl, alkoxy, aryloxy, acyloxy, benzyl, benzyloxy, acetyl, carboxyl, carboxyalkyl, carboxyalkylamido, carboxydialkylamido, carboxamido, alkylcarbonyl, arylamino, diarylamino, nitrile, tolyl, xylyl, mesityl, anisyl, pyrrolidinyl, formyl, dioxane, alkylthiol, heteroaryl, such as pyran, pyrrole, furan, thiophene, thiazole, pyrazole, pyridine, or pyrimidine, phenylcarbonyl, benzylcarbonyl, nitrophenyl, trialkylsilyl, nitro, sulfonyl, nitrobenzyl, trialkylammonium, tetrahydrofuranyl, tetrahydropyranyl, piperdinyl, morpholinyl, halo, cyano, hydroxy, thiol, cycloalkyl, amino, alkylamino, and dialkylamino.

In one aspect, the present invention provides novel nitric oxide-releasing imidate compounds of the formula (II):

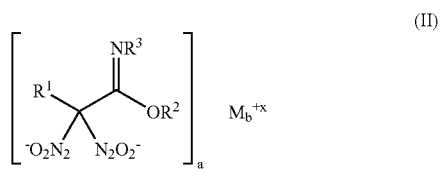

wherein $R^1$ is hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted alkoxy, nitrile, halo, an unsubstituted or substituted benzyl, an unsubstituted or substituted phenyl, an unsubstituted or substituted naphthyl, an unsubstituted or substituted piperazino, an unsubstituted or substituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, an unsubstituted or substituted tolyl, xylyl, anisyl, mesityl, an unsubstituted or substituted acetoxy, carboxy, an unsubstituted or substituted carboxyethyl, an unsubstituted or substituted alkylcarbonyl, thiol, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, an unsubstituted or substituted nitrophenyl, trialkylsilyl or nitro; $R^2$ is an unsubstituted or substituted $C_{1-12}$ straight chain alkyl, an unsubstituted or substituted $C_{3-12}$ branched chain alkyl, a phenyl, or naphthyl; $R^3$ is hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted $C_{3-8}$ cycloalkyl, a $C_{3-8}$ heterocyclic ring, an unsubstituted or substituted naphthyl, an unsubstituted or substituted tetrahydronaphthyl, an unsubstituted or substituted octahydronaphthyl, benzyl or substituted benzyl, or phenyl or substituted phenyl; and $M^{+x}$ is a pharmaceutically acceptable cation, x is the valence of the cation, and a and b are the smallest integers that result in a neutral compound. The substituent $R^1$ can be further substituted with at least one nitric oxide-releasing functional group.

Any one or more of $R^1$, $R^2$, and $R^3$ of formula (II) can be substituted. Generally each of $R^1$, $R^2$, and $R^3$ can have 1 to 3 substituents that are independently selected from the group consisting of alkyl, aryl, such as phenyl or naphthyl, alkoxy, aryloxy, acyloxy, benzyl, benzyloxy, acetyl, carboxyl, carboxyalkyl, carboxyalkylamido, carboxydialkylamido, carboxamido, alkylcarbonyl, arylamino, diarylamino, nitrile, tolyl, xylyl, mesityl, anisyl, pyrrolidinyl, formyl, dioxane, alkylthiol, heteroaryl, such as pyran, pyrrole, furan, thiophene, thiazole, pyrazole, pyridine, or pyrimidine, phenylcarbonyl, benzylcarbonyl, nitrophenyl, trialkylsilyl, nitro, sulfonyl, nitrobenzyl, trialkylammonium, tetrahydrofuranyl, tetrahydropyranyl, piperdinyl, morpholinyl, halo, cyano, hydroxy, thiol, cycloalkyl, amino, alkylamino, and dialkylamino.

Preferably, $R^1$ of the compound of formula (II) is an unsubstituted or substituted aryl. More preferably, $R^1$ of the compound of formula (II) is an unsubstituted or substituted phenyl, and most preferably $R^1$ of the compound of formula (II) is a phenyl, 4-methoxyphenyl, 4-chlorophenyl, or 3,4,5-trimethoxyphenyl. Preferably, $R^2$ of the compound of formula (II) is methyl or ethyl. More preferably, $R^2$ of the compound of formula (II) is methyl. Preferably, $R^3$ of the compound of formula (II) is hydrogen. More preferably, $R^1$ of the compound of formula (II) is an unsubstituted aryl, $R^2$ is methyl, and $R^3$ is hydrogen.

In another aspect, the present invention provides novel nitric oxide-releasing thioimidate compounds of formula (III):

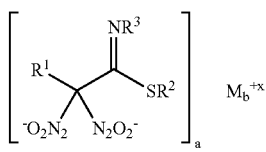

(III)

wherein $R^1$ is hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted alkoxy, nitrile, halo, an unsubstituted or substituted benzyl, an unsubstituted or substituted phenyl, an unsubstituted or substituted naphthyl, an unsubstituted or substituted piperazino, an unsubstituted or substituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, an unsubstituted or substituted tolyl, xylyl, anisyl, mesityl, an unsubstituted or substituted acetoxy, carboxy, an unsubstituted or substituted carboxyethyl, an unsubstituted or substituted alkylcarbonyl, thiol, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, an unsubstituted or substituted nitrophenyl, trialkylsilyl or nitro; $R^2$ is an unsubstituted or substituted $C_{1-12}$ straight chain alkyl, an unsubstituted or substituted $C_{3-12}$ branched chain alkyl, a phenyl, or naphthyl; $R^3$ is hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted $C_{3-8}$ cycloalkyl, a $C_{3-8}$ heterocyclic ring, an unsubstituted or substituted naphthyl, an unsubstituted or substituted tetrahydronaphthyl, an unsubstituted or substituted octahydronaphthyl, benzyl or substituted benzyl, or phenyl or substituted phenyl; and $M^{+x}$ is a pharmaceutically acceptable cation, x is the valence of the cation, and a and b are the smallest integers that result in a neutral compound. The substituent $R^1$ can be further substituted with at least one nitric oxide-releasing functional group.

Any one or more of $R^1$, $R^2$, and $R^3$ of formula (III) can be substituted. Generally each of $R^1$, $R^2$, and $R^3$ can have 1 to 3 substituents that are independently selected from the group consisting of alkyl, aryl, such as phenyl or naphthyl, alkoxy, aryloxy, acyloxy, benzyl, benzyloxy, acetyl, carboxyl, carboxyalkyl, carboxyalkylamido, carboxydialkylamido, carboxamido, alkylcarbonyl, arylamino, diarylamino, nitrile, tolyl, xylyl, mesityl, anisyl, pyrrolidinyl, formyl, dioxane, alkylthiol, heteroaryl, such as pyran, pyrrole, furan, thiophene, thiazole, pyrazole, pyridine, or pyrimidine, phenylcarbonyl, benzylcarbonyl, nitrophenyl, trialkylsilyl, nitro, sulfonyl, nitrobenzyl, trialkylammonium, tetrahydrofuranyl, tetrahydropyranyl, piperdinyl, morpholinyl, halo, cyano, hydroxy, thiol, cycloalkyl, amino, alkylamino, and dialkylamino.

Preferably, $R^1$ of the compound of formula (III) is an unsubstituted or substituted aryl. More preferably, $R^1$ of the compound of formula (III) is an unsubstituted or substituted phenyl, and most preferably $R^1$ of the compound of formula (III) is a phenyl, 4-methoxyphenyl, 4-chlorophenyl, or 3,4,5-trimethoxyphenyl. Preferably, $R^2$ of the compound of formula (III) is methyl or ethyl. More preferably, $R^2$ of the compound of formula (III) is methyl. Preferably, $R^3$ of the compound of formula (III) is hydrogen. More preferably, $R^1$ of the compound of formula (III) is an unsubstituted aryl, $R^2$ is methyl, and $R^3$ is hydrogen.

The counterion, $M^{+x}$, is any pharmaceutically acceptable counterion. The only requirement for the pharmaceutically acceptable counterion chosen is biological compatability in an animal, such as a human. Biologically acceptable counterions include alkali metals such as sodium ion, potassium ion, lithium ion, and the like; alkaline earth metals such as magnesium ion, calcium ion, and the like; Group III metals such as aluminum ion; Group IV metals such as tin ion; and transition metals, including iron ion, copper ion, manganese ion, zinc ion, cobalt ion, vanadium ion, molybdenum ion, platinum ion, and the like. Non-metal counterions include quaternary ammonium ions. Metal ions that may be considered toxic may, nevertheless, be pharmaceutically acceptable and thus within the scope of the invention if their complexes with the diazeniumdiolates are sufficiently potent pharmacologically and the total concentration of the metal counterion upon dosing is below the toxic threshold of the metal.

In another aspect, the invention provides a method of preparing a nitric oxide-releasing compound of formula (I) from a compound not containing an imidate or thioimidate group, as illustrated in Equation 1. In the preparation of an imidate diazeniumdiolate, the method comprises (a) contacting a nitrile of the formula $R^1CH_2CN$ with a metal alkoxide and an alcohol (e.g., NaOMe/HOMe); and (b) contacting the product of (a) with nitric oxide to form a diazeniumdiolated nitrile compound; (c) contacting the diazeniumdiolated nitrile compound with an alkoxide to form the imidate of formula (II), for example, where $R^1$ is discussed herein. Similarly, in the preparation of a thioimidate diazeniumdiolate, the method comprises (a) contacting a nitrile of the formula $R^1CH_2CN$ with a metal thiolate and a thiol (e.g., NaSMe/HSMe); and (b) contacting the product of (a) with nitric oxide to form a diazeniumdiolated nitrile compound; (c) contacting the diazeniumdiolated nitrile compound with a thiolate to form the thioimidate of formula (III), wherein $R^1$ is discussed herein. These methods in accordance with the invention are useful for preparing a (thio)imidate diazeniumdiolate in which the NO-releasing $N_2O_2^-$ functional groups are bound to a carbon atom rather than nitrogen.

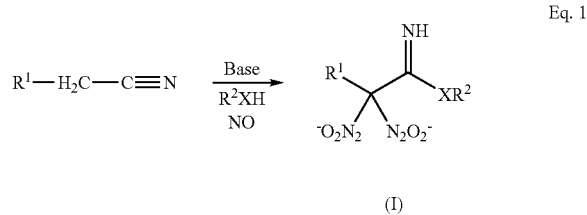

Eq. 1

(I)

wherein X is O or S.

While typically the reaction to form the diazeniumdiolated imidates proceeds as described above, it is recognized that in some cases formation of the imidate may precede attachment of the diazeniumdiolate group. The exact sequence of the reaction is of no consequence to the ultimate goals of the invention and should in no way be construed to limit its scope.

While not wishing to be bound by any particular theory, it is believed that the nitrile $R^1CH_2CN$, in the presence of alkoxide or thiolate, forms a carbanion. This carbanion forms a bis-diazeniumdiolate compound in the presence of nitric oxide gas. Once the diazeniumdiolated nitrile compound is formed, the alkoxide or thiolate produces the corresponding imidate or thioimidate diazeniumdiolate.

Imidate and thioimidate diazeniumdiolates of formulae (I), (II), and (III) are useful as intermediate compounds in order to prepare derivative diazeniumdiolate compounds with medicinal uses. Substituted nitric oxide-releasing thioimidates of formula (III) can be prepared by a method comprising (a) contacting a nitrile of the formula $R^1CH_2CN$ with a metal alkoxide and an alcohol; (b) contacting the product of (a) with NO to form a diazeniumdiolated nitrile compound; (c) contacting the diazeniumdiolated nitrile compound with an alkoxide and alcohol (e.g., NaOMe/HOMe); and (d) contacting the product of (c) with a thiol-substituted compound to form a substituted nitric oxide-releasing thioimidate of formula (III). The thiol-substituted compound can be, for example, L-cysteine, a protein, an enzyme, such as glutathione, or a thiol-modified substrate. In a similar reaction, a primary amine-substituted compound may be used in place of the thiol-substituted compound (e.g., L-lysine) in (d), in order to form an NO-releasing amidine.

In another aspect, the present invention provides novel nitric oxide-releasing amide compounds of formula (IV):

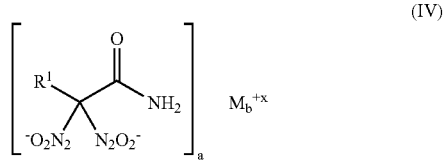

wherein $R^1$ is hydrogen, an unsubstituted or substituted $C_{1-12}$ straight chain alkyl, an unsubstituted or substituted $C_{1-12}$ branched chain alkyl, an unsubstituted or substituted $C_{3-12}$ straight chain alkenyl, an unsubstituted or substituted $C_{3-12}$ branched chain alkenyl, an unsubstituted or substituted alkoxy, nitrile, halo, an unsubstituted or substituted benzyl, an unsubstituted or substituted phenyl, an unsubstituted or substituted naphthyl, an unsubstituted or substituted piperazino, an unsubstituted or substituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, an unsubstituted or substituted tolyl, xylyl, anisyl, mesityl, an unsubstituted or substituted acetoxy, carboxy, an unsubstituted or substituted carboxyethyl, an unsubstituted or substituted alkylcarbonyl, thiol, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, an unsubstituted or substituted nitrophenyl, trialkylsilyl or nitro; and $M^{+x}$ is a pharmaceutically acceptable cation, x is the valence of the cation, and a and b are the smallest integers that result in a neutral compound. The substituent $R^1$ can be further substituted with at least one nitric oxide-releasing functional group.

The substituent $R^1$ of formula (IV) can be substituted with 1 to 3 substituents that are independently selected from the group consisting of alkyl, aryl, such as phenyl or naphthyl, alkoxy, aryloxy, acyloxy, benzyl, benzyloxy, acetyl, carboxyl, carboxyalkyl, carboxyalkylamido, carboxydialkylamido, carboxamido, alkylcarbonyl, arylamino, diarylamino, nitrile, tolyl, xylyl, mesityl, anisyl, pyrrolidinyl, formyl, dioxane, alkylthiol, heteroaryl, such as pyran, pyrrole, furan, thiophene, thiazole, pyrazole, pyridine, or pyrimidine, phenylcarbonyl, benzylcarbonyl, nitrophenyl, trialkylsilyl, nitro, sulfonyl, nitrobenzyl, trialkylammonium, tetrahydrofuranyl, tetrahydropyranyl, piperdinyl, morpholinyl, halo, cyano, hydroxy, thiol, cycloalkyl, amino, alkylamino, and dialkylamino.

In addition, a bis-diazeniumdiolated amide compound of formula (IV) can be prepared from an imidate diazeniumdiolate of formula (II). Substituted nitric oxide-releasing amides of formula (IV) can be prepared by a method comprising (a) contacting a nitrile of the formula $R^1CH_2CN$ with a metal alkoxide and an alcohol; (b) contacting the product of (a) with NO to form a diazeniumdiolated nitrile compound; (c) contacting the diazeniumdiolated nitrile compound with an alkoxide and alcohol (e.g., NaOMe/HOMe); and (d) contacting the product of (c) with hydroxide ion to form a substituted nitric oxide-releasing amide of formula (IV), wherein $R^1$ is discussed herein. Preferably the hydroxide ion source is water, a Group I or II hydroxide (e.g., NaOH, KOH, $Mg(OH)_2$), or combinations thereof. Alternatively, the bis-diazeniumdiolated amide of formula (IV) can be prepared by direct hydrolysis of the diazeniumdiolated nitrile compound. The method comprises (a) contacting a nitrile of the formula $R^1CH_2CN$ with a metal alkoxide and an alcohol; (b) contacting the product of (a) with NO to form a diazeniumdiolated nitrile compound; (c) contacting the diazeniumdiolated nitrile compound with hydroxide ion to form a substituted nitric oxide-releasing amide of formula (IV), wherein $R^1$ is discussed herein.

Any combination of metal alkoxide/alcohol or metal thiolate/thiol system that is capable of reaction with a nitrile to form an imidate or thioimidate when exposed to NO, results in the compounds, which are within the scope of the invention. Suitable metal alkoxides are of the formula $MOR^2$, wherein M and $R^2$ are as discussed above. Suitable alcohols are of the formula $HOR^2$, wherein $R^2$ is as discussed above. The substituent $R^2$ of the metal alkoxide and the alcohol can be the same or different. Preferably, $R^2$ of the metal alkoxide and the alcohol are the same. Similarly, suitable metal thiolates are of the formula $MSR^2$, wherein M and $R^2$ are as discussed above. Suitable thiols are of the formula $HSR^2$, wherein $R^2$ is as discussed above. The substituent $R^2$ of the metal thiolate and the thiol can be the same or different. Preferably, $R^2$ of the metal thiolate and the thiol are the same. Also included in the invention are modifications to the above-described syntheses such as, for example, the use of a metal hydroxide in combination with an alcohol (e.g., $MOH/HOR^2$). Combinations of metal hydroxides and metal alkoxides with an alcohol can also be used.

The nitriles of Equation 1 result in imidate and thioimidate diazeniumdiolates of formulae (I), (II), and (III) upon exposure to nitric oxide gas. To prepare the diazeniumdiolates of the present invention, nitrile, imidate, or thioimidate compounds are exposed to nitric oxide gas at a nitric oxide gas pressure as low as about 1 atm. Preferably, the pressure is at least about 1 atm, and more preferably, it is at least about 2 atm.

In another aspect, the invention provides compositions, including pharmaceutical compositions, comprising the novel imidate diazeniumdiolates, the novel thioimidate diazeniumdiolates, the novel amide diazeniumdiolates or combinations thereof. Preferably, the pharmaceutical compositions further comprise a pharmaceutically acceptable carrier.

One skilled in the art will appreciate that suitable methods of administering a diazeniumdiolate composition of the present invention to an animal, e.g., a mammal such as a human, are known, and, although more than one route can be used to administer a particular composition, a particular route can provide a more immediate and more effective reaction than another route. Pharmaceutically acceptable carriers are also well known to those who are skilled in the art. The choice of carrier will be determined, in part, both by the particular composition and by the particular method used to administer the composition. Accordingly, there is a wide variety of suitable formulations of the pharmaceutical compositions of the present invention.

Formulations suitable for oral administration can consist of (a) liquid solutions, such as an effective amount of the diazeniumdiolate dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The diazeniumdiolates of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compositions employed (taking into consideration, at least, the rate of NO evolution, the extent of NO evolution, and the bioactivity of any decomposition products derived from the diazeniumdiolates) and the condition of the animal (e.g., human), as well as the body weight of the animal (e.g., human) to be treated. The size of the dose also will be determined by the existence, nature, and extent of any adverse side effects that might accompany the administration of a particular composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration of thioimidate or imidate diazeniumdiolates in pharmaceutical compositions for topical administration is 0.05 to 15% (by weight). A preferred concentration is from 0.02 to 5%. A more preferred concentration is from 0.1 to 3%.

Nitric oxide-releasing imidates, thioimidates, and amides are useful for the therapeutic treatment of many biological disorders. For example, thioimidate diazeniumdiolates are useful as fungicides (buthiobate) and in drug design for anticancer therapy. Reaction with amines will produce novel amidines of a class of compounds known for their antiviral, antibacterial, antifungal, and antiprotozoal properties.

The present invention also provides methods of using a nitric oxide-releasing diazeniumdiolate of formula (I), (II), (III) or (IV) of the invention or a substituted thioimidate diazeniumdiolate of the present invention. In one embodiment, a method of treating an animal, e.g., a mammal such as a human, with a biological disorder treatable with nitric oxide, is provided. The method comprises administering to the animal (e.g., human) in need thereof an amount of a diazeniumdiolate of formula (I), (II), (III) or (IV) of the invention, a substituted thioimidate diazeniumdiolate of the present invention, or compositions thereof sufficient to treat the biological disorder in the animal (e.g., human). In this embodiment, "biological disorder" can be any biological disorder, including hypertension, sickle cell anemia, leishmania, restenosis, cancer, impotency, platelet aggregation, and a biological disorder due to a genetic defect or infection with an infectious agent, such as a virus, bacterium, fungus or parasite, as long as the disorder is treatable with nitric oxide.

The diazeniumdiolates of the invention are useful for treating an animal, e.g., a mammal such as a human, for infection with, for example, a virus, a bacterium, or a parasite. The method comprises administering to the animal, e.g., human, an amount of a diazeniumdiolate of formula (I), (II), (III) or (IV) of the invention, a substituted thioimidate diazeniumdiolate of the present invention, or compositions thereof sufficient to treat the infection in the animal.

The diazeniumdiolates of formula (I), (II), (III) or (IV) of the invention, a substituted thioimidate diazeniumdiolate of the present invention, or compositions thereof are useful for treating an animal, e.g., a mammal such as a human, for cancer. The method comprises administering to the animal, e.g., human, an amount of a diazeniumdiolate of formulae of formula (I), (II), (III) or (IV) of the invention, a substituted thioimidate diazeniumdiolate of the present invention, or compositions thereof sufficient to prevent the growth or metastasis of the cancer in the animal (e.g., human) or to render it more susceptible to radiation or chemotherapy.

The imidate and thioimidate diazeniumdiolates of the invention are useful for treating an inanimate object for the presence of a potentially infectious virus, bacterium, or parasite. The method comprises contacting the inanimate object with an amount of an diazeniumdiolate of formula (I), (II), (III) or (IV) of the invention, a substituted thioimidate diazeniumdiolate of the present invention, or compositions thereof sufficient to reduce the presence of the potentially infectious virus, bacterium or parasite. By "potentially infectious" is meant the capability of infecting an animal, e.g., a mammal such as a human.

The present invention provides a method of treating sickle cell anemia with an imidate or thioimidate diazeniumdiolate of formula (I), (II) or (III) or compositions thereof. By way of example and not in limitation of the invention, the imidate diazeniumdiolate of 1,4-phenylenediacetonitrile is useful in the treatment of sickle cell anemia. The compound 1,4-phenylenediacetonitrile is converted to the nitric oxide-releasing imidate by reaction with NO gas in alcoholic sodium methoxide as illustrated by Equation 2.

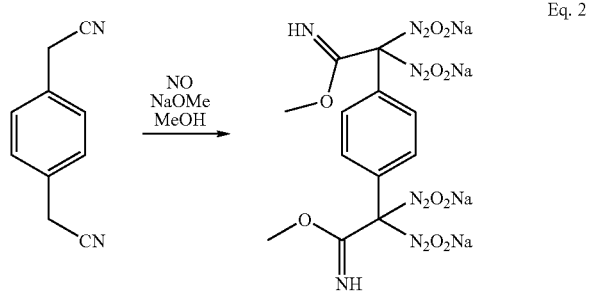

Eq. 2

Compounds of the present invention and compositions thereof are useful for the treatment of leishmania. The present invention provides a method of treating leishmania by administering an effective amount of a compound of formula (I), (II), (III) or (IV) of the invention, a substituted thioimidate diazeniumdiolate of the present invention, or compositions thereof. Preferably, the NO-releasing protein is cross-linked to the tubulin protein. The cross-linking molecule is preferably chosen to disrupt tubulin polymerization and the release of NO would augment the NO produced from the macrophages and impair the ability of the parasite to form microtubules via nitration.

In another aspect of the invention, the metabolites of the organic moiety of the diazeniumdiolate compounds of the present invention have medicinal purposes as well. After the diazeniumdiolate compound of formula (I), (II), (III) or (IV) of the invention or substituted thioimidate diazeniumdiolate of the present invention release NO under physiological conditions, part of the organic moiety (e.g., the $N_2O_2$ group) decomposes and the decomposition product, an oxime (hydroximino compound) in many cases, has medicinal purposes (e.g., fungicidal). See, e.g., U.S. Pat. Nos. 5,264,484 and 4,874,786, S.U. Patent No. 1,094,273, J.P. Patent No. 05148104, D.E. Patent No. 2616089, and Massolini, et al., *Farmaco, Ed. Sci.*, 42(2), 117–124 (1987), which are incorporated by reference. Therefore, the compounds of the present invention serve a dual purpose: one in which the release of NO is beneficial and another in which the metabolite is medicinally useful.

Organic polymer beads with a free amino group are capable of reacting with nitric oxide releasing imidates to form nitric oxide releasing polymers. Organic polymer beads are currently used to immobilize proteins to their surface via cross-linking reagents. Organic polymer beads are ideal for reaction with the nitric oxide-releasing imidates to generate polymers that can be a steady source of nitric oxide. The conditions used to form the amidine linkage, typically pH of about 8.0–9.0 and room temperature, are well suited to the imidate diazeniumdiolates of the invention because the diazeniumdiolate groups are stable in that environment. Nitric oxide-releasing polymers have extensive applications in the biomedical field as medical devices based upon the novel properties of nitric oxide.

The nitric oxide-releasing functional group can also be that of a polymer, e.g., a nitric oxide-releasing imidate/thioimidate/amide bound to a polymer, similar to those described in, for example, U.S. Pat. Nos. 5,405,919, 5,525,357, 5,632,981, 5,650,447, 5,676,963, 5,691,423, and 5,718,892, and incorporated herein by reference. By "bound to a polymer" it is meant that the nitric oxide-releasing imidate/thioimidate/amide, such as those described by formulae (I)–(IV) is associated with, part of, incorporated with, or contained within the polymer matrix physically or chemically. Physical association or bonding of the nitric oxide-releasing imidate/thioimidate/amide to the polymer may be achieved by co-precipitation of the polymer with the nitric oxide-releasing imidate/thioimidate/amide as well as by covalent bonding of the complex to the polymer. Chemical bonding of the nitric oxide-releasing imidate/thioimidate/amide to the polymer may be by, for example, covalent bonding of the imidate/thioimidate moiety of the nitric oxide-releasing imidate/thioimidate/amide to the polymer such that the imidate/thioimidate/amide residue to which the NONO group is attached forms part of the polymer itself, i.e., is in the polymer backbone, or is attached to a group or groups pendant to the polymer backbone. If the diazeniumdiolates of the present invention are chemically bound to the polymer/biopolymer, then the diazeniumdiolates are bound to the polymer/biopolymer by at least one functional group on the polymer or biopolymer. Preferably, more than one diazeniumdiolate compound of the present invention is chemically bound per molecule of the polymer/biopolymer. The manner in which the nitric oxide-releasing imidate/thioimidate/amide is associated, part of, or incorporated with or contained within, i.e., "bound" to the polymer, is inconsequential to the invention and all means and degrees of association, incorporation or bonding are contemplated herein.

Any of a wide variety of polymers can be used in the context of the invention. Illustrative of polymers suitable for use in the invention are polyolefins, such as polystyrene, polypropylene, polyethylene, polytetrafluorethylene, polyvinyl chloride, polyvinylidene difluoride, and polyethers such as polyethylene glycol, polysaccharides such as dextran, polyesters such as poly(lactide/glycolide), polyamides such as nylon, polyurethanes, polyethylenimine, biopolymers such as peptides, polypeptides, enzymes, polysaccharides, proteins, oligonucleotides, antibodies and nucleic acids, starburst dendrimers, and the like. For example, chitosan is a polysaccharide containing numerous primary amine groups. The term "biopolymers", as used herein, also include monomeric units of larger biopolymers such as monosaccharides, amino acids or nucleotides.

The advantage of preparing diazeniumdiolate compounds bound to a (bio)polymer by the methods of the present invention is that the diazeniumdiolate compound is formed first and then bound to the polymer. This methods enables a whole new class of compounds to be prepared because the (bio)polymer is not directly exposed to the potentially deleterious effects of nitric oxide gas or any nitrogen oxide that might form therefrom in the presence of oxygen.

The imidate diazeniumdiolate compounds of formula (II) also serve as cross-linking agents. Homobifunctional imidates are known in the art to serve as cross-linkers, particularly in the cross-linking of proteins. See, e.g., Ahmadi, et al. *FEBS Lett.* 94(2), 365–367 (1978); Brandon, *Cellular and Molecular Biology* 26, 569–573 (1980), Brew, et al., *J. Biol. Chem.*, 250(4) 1434–1444 (1975). Bifunctional imidate diazeniumdiolates are within the scope of the present invention, such as, in non-limiting examples, where R is a nitrile or alkyl group substituted with a nitrile. The methods of preparing such bifunctional imidate diazeniumdiolates are the same as those for preparing compounds of formula (II), which are described herein. The bifunctional imidate diazeniumdiolate can cross-link any suitable compound, such as a polymer or biopolymer described herein. The cross-linking can occur either between more than one compound (e.g., two polymer chains) or between sites within the same molecule.

Another aspect of this invention includes a method for preparing a nitric oxide-releasing imidate/thioimidate/amide that is capable of being bound to a substrate, where the method includes contacting the diazeniumdiolate with a substrate. Preferably the substrate has moieties that allow for chemical bonding of the NO-releasing imidate/thioimidate/amide to the substrate. See, for example, U.S. patent application Ser. No. 2001/0003599, which is incorporated herein in its entirety. In a specific example, a stainless steel coupon can be treated such that free thiol groups reside on the surface. An NO-releasing imidate of formula (II) can be reacted with the stainless steel coupon to form a substrate coated with an NO-releasing substituted thioimidate.

The substrate can be of any suitable biocompatible material, such as metal, glass, ceramic, or plastic or rubber. Preferably, the substrate is metal. The substrate used in the preparation of the medical device can be derived from any suitable form of a biocompatible material, such as, for example, a sheet, a fiber, a tube, a fabric, an amorphous solid, an aggregate, dust or the like.

Metal substrates suitable for use in the invention include, for example, stainless steel, nickel, titanium, tantalum, aluminum, copper, gold, silver, platinum, zinc, silicon, magnesium, tin, alloys, coatings containing any of the above and combinations of any of the above. Also included are such metal substrates as galvanized steel, hot dipped galvanized steel, electrogalvanized steel, annealed hot dipped galvanized steel and the like. Preferably, the metal substrate is stainless steel.

Glass substrates suitable for use in the invention include, for example, soda lime glass, strontium glass, borosilicate glass, barium glass, glass-ceramics containing lanthanum as well as combinations thereof.

Ceramic substrates suitable for use in the invention include, for example, boron nitrides, silicon nitrides, aluminas, silicas, combinations thereof, and the like.

Plastic substrates suitable for use in the invention include, for example, acrylics, acrylonitrile-butadiene-styrene, acetals, polyphenylene oxides, polyimides, polystyrene, polypropylene, polyethylene, polytetrafluoroethylene, polyvinylidene, polyethylenimine, polyesters, polyethers, polylactones, polyurethanes, polycarbonates, polyethylene terephthalate, as well as copolymers and combinations thereof. Typical rubber substrates suitable for use in the invention include, for example, silicones, fluorosilicones, nitrile rubbers, silicone rubbers, fluorosilicone rubbers, polyisoprenes, sulfur-cured rubbers, isoprene-acrylonitrile rubbers, and the like. Silicones, fluorosilicones, polyurethanes, polycarbonates, polylactones, and mixtures or copolymers thereof are preferred plastic or rubber substrates because of their proven bio- and hemocompatability when in direct contact with tissue, blood, blood components, or bodily fluids.

Other suitable substrates include those described in WO 00/63462, and incorporated herein by reference.

The invention provides medical devices which are capable of releasing nitric oxide when in use, but which are otherwise inert to nitric oxide release. In particular, NO-releasing functional groups are bound to a substrate that is coated with an imidate or thioimidate diazeniumdiolate. The term "bound" as used herein includes covalent bonds, ionic bonds, van der Waal forces, hydrogen bonding, electrostatic bonding, and all other methods for attaching organic chemical functional groups to a substrate.

A "medical device" refers to any device having surfaces that contact tissue, blood, or other bodily fluids in the course of their use or operation, which are found in or are subsequently used in patients or animals. Medical devices include, for example, extracorporeal devices for use in surgery, such as blood oxygenators, blood pumps, blood storage bags, blood collection tubes, blood filters including filtration media, tubing used to carry blood and the like which contact blood which is then returned to the patient or animal. Medical devices also include endoprostheses implanted in a human or animal body, such as vascular grafts, stents, pacemaker leads, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts.

The following examples further illustrate the invention but, of course, should not be construed as in any way limiting its scope.

The nitrites and all solvents were purchased from Aldrich Chemical Company (Milwaukee, Wis.). Nitric oxide was obtained form Matheson Gas Products (Montgomeryville, Pa.). The $^1$H NMR and $^{13}$C NMR spectra were recorded in $D_2O$ ($^1$H at 300 MHz; $^{13}$C at 75 MHz). Ultraviolet spectra (10 mM NaOH unless otherwise specified) and kinetic information were obtained on a Hewlett Packard 8452A UV-visible spectrophotometer with a thermostated cell holder. Infrared data was recorded on a Perkin-Elmer 1430 infrared spectrometer. Nitric oxide was measured with a Thermal Energy Analyzer model 502A (Thermedics, Inc., Woburn, Mass.). Melting points are uncorrected. Elemental analyses were performed by Atlantic Microlab, Inc. (Norcross, Ga.).

EXAMPLE 1

This Example describes a generalized procedure for the preparation of nitric oxide (NO) and or nitroxyl ($NO^-$) releasing imidates from nitrites.

The appropriate nitrile was dissolved in methanol and 2 equivalents of metal alkoxide (25% sodium methoxide solution unless otherwise noted) were added. The solution was placed in a standard high pressure Parr® bottle. Argon was passed through the solution for 10 minutes before attachment to the NO apparatus. A complete description of these pressure reactions has been given in Hrabie et al. (*J. Org. Chem.* 58: 1472–1476 (1993)). The Parr® bottle was then alternately pressurized to 1.4 atm (20 psi) with high purity argon and vented for a total of ten cycles. The vessel was then pressurized to 2.7 atm (40 psi) with NO gas while stirring at room temperature. Additional NO was added as needed. When the consumption of NO was complete, usually within about 24 hours, excess NO gas was vented, and the system was purged with argon. The product was isolated by filtration, washed with diethyl ether, and dried in vacuo. A crystalline material can be obtained by dissolution of the powder in a minimum amount of water and addition of a methanol-ether mixture until turbid. Crystallization occurs at 4° C. overnight.

EXAMPLE 2

This Example describes the preparation of benzyl diazeniumdiolate methoxy imidate.

Benzyl cyanide (5 mL, 0.043 mol) was dissolved in 50 mL methanol in a pressure bottle, and 2 equivalents of sodium methoxide (19.6 mL, 0.086 mol) were slowly added. The solution was reacted with NO gas for 24 hours and the product was isolated as a hydrate. Yield 5.25 g (35%); UV $\lambda_{max}$=264 nm ($\epsilon$=14.0 $mM^{-1}$ $cm^{-1}$); Mp chars above 250° C.; $^1$H NMR (300 MHz, $D_2O$) 3.8 ppm (s, 3H), 7.2–7.6 ppm (m, 5H). Anal. Calcd for $C_9H_9N_5O_5$x2$H_2O$: C, 30.95; H, 3.75; N, 20.05. Found: C, 30.65; H, 3.85; N, 19.79.

EXAMPLE 3

This Example describes the preparation of benzyl bis diazeniumdiolate ethoxy imidate.

Benzyl cyanide (3 mL, 0.025 moles) was dissolved in 30 mL of ethanol, and 2 equivalents of potassium ethoxide (4.30 g, 0.051 moles) were added. The reaction was run as described in Example 1. A light tan product was obtained. Yield 4.48 g, 50%; Mp 150° C. dec.; UV $\lambda_{max}$ ($\epsilon$) 262 nm (13.6 $mM^{-1}$ $cm^{-1}$); $^1$H NMR (300 MHz, $D_2O$): 1.27 (t, 3H), 4.26 (q, 2H), 7.47 ppm (s, 5H). Anal. Calcd for $C_{10}H_{11}N_5K_2O_5$: C, 33.42; H, 3.08; N, 19.49. Found: C, 33.48; H, 3.08; N, 19.17.

EXAMPLE 4

This Example describes the preparation of a derivative of benzyl diazeniumdiolate methoxy imidate with an electron donating substituent on the ring.

4-Methoxybenzyl cyanide (5 mL, 0.036 moles) was mixed with 50 mL methanol, and 25% sodium methoxide (16.8 mL, 0.072 moles) was added. The NO reaction was conducted as described in Example 1, and a white powder was obtained as a hydrate. Yield 1.57 g, 11%; Mp 140° C. dec.; UV $\lambda_{max}$ ($\epsilon$) 262 nm (14.6 $mM^{-1}$ $cm^{-1}$); $^{13}$C NMR (75 MHz, $D_2O$): 57.34, 58.28, 99.15, 116.67 (2C), 127.38, 133.14 (2C), 162.71, 168.13 ppm. $^1$H NMR (300 MHz, $D_2O$): 3.85 (s, 3H), 3.87 (s, 3H), 7.01–7.40 ppm (AA'BB' 4H). Anal. Calcd for $C_{10}H_{17}N_5Na_2O_9$: C, 30.23; H, 4.31; N, 17.63. Found: C, 30.44; H, 4.22; N, 17.31.

EXAMPLE 5

This Example describes the preparation of a derivative of benzyl bis diazeniumdiolate methoxy imidate with an electron withdrawing substituent on the ring.

A solution of 4-chlorobenzyl cyanide (5 mL, 0.042 moles) was mixed with 50 mL of methanol, and 25% sodium methoxide (20 mL, 0.084 moles) was added. The solution was allowed to react with 2.7 atm (40 psi) of NO gas overnight. Yield 6.92 g, 43%; UV $\lambda_{max}$ ($\epsilon$) 262 nm (14.5 $mM^{-1}$ $cm^{-1}$); $^{13}$C NMR (75 MHz, $D_2O$): 57.44, 98.73, 131.30 (2C), 133.09(2C), 133.94, 138.16, 167.69 ppm. $^1$H NMR (300 MHz, $D_2O$): 3.83 (s, 3H), 7.40–7.49 (m, 4H). Anal. Calcd for $C_9H_{10}ClN_5Na_2O_6$: C, 29.56; H, 2.76; N, 19.15. Found: C, 29.42; H, 2.92; N, 18.89.

EXAMPLE 6

This Example describes the preparation of benzyl diazeniumdiolate nitrile and its subsequent conversion to an imidate.

Benzyl cyanide (3 mL, 0.025 moles) was mixed with 25 mL THF and 10 mL of a 1.0 M solution of trimethylsilanoate sodium salt (10 mL, 0.01 moles) was added. After reaction with NO gas for 24 hours, the precipitate was filtered, washed, and dried. Yield 1.6 g, 100%; mp=192–195° C.; UV $\lambda_{max}$ ($\epsilon$) 266 nm (12.5 $mM^{-1}$ $cm^{-1}$); IR; (KBr pellet) 2240 $cm^{-1}$; $^{13}$C NMR (75 MHz, $D_2O$): 94.08, 116.86, 130.53 (2C), 132.03 (2C), 133.25, 134.07 (2C) ppm. $^1$H NMR (300 MHz, $D_2O$): 7.58 (s, 5H).

A sample of the bis diazeniumdiolated product thus obtained (100 mg) was then dissolved in a minimum of water (0.5 mL) and diluted with methanol (5 mL). Then 5 drops of 25% sodium methoxide were added and the solution was allowed to stir at room temperature overnight. Diethyl ether was added until the solution was turbid at which point it was allowed to precipitate in the refrigerator at 4° C. The product, identified by NMR and IR spectra, was identical to the diazeniumdiolated methoxy imidate produced in Example 2.

EXAMPLE 7

This Example describes the conversion of benzyl diazeniumdiolate ethoxy imidate to benzyl diazeniumdiolate methoxy imidate.

Benzyl diazeniumdiolate ethoxy imidate was synthesized as described in Example 3, dissolved in a minimum amount of water (0.5 mL), and diluted with methanol (5.0 mL). The solution was stirred at room temperature overnight. Diethyl ether was used to precipitate out the benzyl diazeniumdiolated methoxy imidate overnight at 4° C. Conversion was quantitative.

EXAMPLE 8

This Example describes the conversion of 3,4,5-trimethoxy benzyl diazeniumdiolate methoxy imidate to 3,4,5-trimethoxy benzyl diazeniumdiolate amide.

A solution of 3,4,5-trimethoxybenzyl cyanide (2.00 g, 0.0096 moles) in 10 mL methanol was treated with 25% sodium methoxide (4.41 mL, 0.019 moles). The solution was degassed and exposed to 2.7 atm (40 psi) of NO gas for 6 hours. After filtration, the crude material was dissolved in water (2 mL), which converted the imidate to the amide in situ overnight. Yield 1.06 g, 26%; mp=187–190° C.; UV $\lambda_{max}$ ($\epsilon$) 258 nm (broad) (11.0 mM$^{-1}$ cm$^{-1}$); $^{13}$C NMR (75 MHz D$_2$O): 57.35, 58.97, 59.11, 63.74, 93.75, 98.85, 108.43, 109.41, 116.67, 129.46, 131.65, 140.50, 154.85, 155.44, 167.79 ppm. $^1$H NMR (300 MHz D$_2$O): 3.85 (s, 3H), 3.89 (s, 6H), 6.93 (s, 2H). Anal. Calcd for C$_{11}$H$_{17}$N$_5$Na$_2$O$_{10}$: C, 31.07; H, 4.03; N, 16.47. Found: C, 31.37; H, 4.05; N, 16.29.

EXAMPLE 9

This Example describes the conversion of 1-naphthyl diazeniumdiolate imidate to 1-naphthyl diazeniumdiolate amide.

1-Naphthylacetonitrile (2.36 g, 0.014 moles) was dissolved in 25 mL of methanol, and 25% sodium methoxide (6.45 mL, 0.028 moles) was added. The solution was allowed to react with NO gas at 2.7 atm (40 psi) overnight and was then filtered. The product was dissolved in water and precipitated with methanol/ether in the refrigerator. Yield 1.07 g, 20%; mp 130° C. dec.; UV $\lambda_{max}$ ($\epsilon$) 274 nm (17.1 mM$^{-1}$ cm$^{-1}$); $^{13}$C NMR (75 MHz, D$_2$O): 94.31, 116.21, 125.88, 127.82, 128.53, 129.32, 129.45, 130.62, 131.83, 132.31, 135.28, 136.50 ppm. $^1$H NMR (300 MHz, D$_2$O): 7.39–8.14 ppm (m, 7.5H). Anal. Calcd for C$_{12}$H$_{13}$N$_5$Na$_2$O$_7$: C, 37.41; H, 3.40; N, 18.18; Na, 11.94. Found: C, 37.92; H, 3.50; N, 17.95; Na, 11.82.

EXAMPLE 10

This Example describes the reaction between an NO releasing imidate and an amino acid to form an NO-releasing substituted thioimidate.

The benzyl diazeniumdiolated imidate (1.46 g, 0.0042 moles) was dissolved in 3 mL 0.01 mM NaOH and mixed with a solution of L-cysteine (5.0 g in 20 mL 0.01 mM NaOH) at room temperature. The solution turned light pink, and a precipitate appeared after several minutes. After 24 hours, the solution was filtered, washed with ether, and dried in vacuo. Yield: 1.78 g. NO release in pH 7.4 buffer at 37° C. from the product was measured qualitatively.

EXAMPLE 11

This Example illustrates the production of NO and N$_2$O by diazeniumdiolated imidates.

For the detection of NO, selected compounds from the examples were dissolved in either pH 7.4 buffer or 10% H$_2$SO$_4$, and the headspace was swept with argon into a chemiluminescence detector. The detection of nitrous oxide (N$_2$O), formed from the dimerization and dehydration of HNO, was done by gas chromatography in both pH 7.4 buffer and 0.1 M HCl. The results are shown in Table 1.

| Compound from Example | Solution | NO (mole gas/mole cmpd) | N$_2$O (mole gas/mole cmpd |
|---|---|---|---|
| 2 | pH 7.4 | 0.36 | — |
| 2 | acid | 0.46 | 1.52 |
| 4 | pH 7.4 | 0.34 | 1.08 |
| 4 | acid | 0.19 | 1.07 |
| 5 | pH 7.4 | 0.38 | 1.06 |
| 9 | pH 7.4 | 0.16 | — |
| 9 | acid | 0.02 | — |

EXAMPLE 12

This Example illustrates the measurement of the rate of NO releasing decay of diazeniumdiolate imidates in solution.

A stock solution of the NO releasing imidate in 10 mM NaOH was prepared. A quartz cuvette was filled with 3 mL of pH 7.4 phosphate buffer and fitted to a thermostated cell holder in the UV-visible spectrophotometer. A stirring bar was added to the cell to provide sample homogeneity. After 5 minutes of equilibration to 25° C., an aliquot of the stock solution (10 μl) was injected into the cuvette to initiate the kinetic experiment. The NO releasing imidates generally show good first order decay kinetics. The half-life data for selected compounds is shown in Table 2.

| Compound from Example | $t_{1/2}$ (seconds) |
|---|---|
| 2 | 738 |
| 4 | 113 |
| 5 | 198 |

EXAMPLE 13

This Example describes the conversion of acetonitrile to an NO-releasing imidate.

A solution of 100 mL acetonitrile and 10 mL (0.043 moles) 25% sodium methoxide is degassed and placed under 2.7 atm (40 psi) of NO gas. An off-white product is obtained overnight, which is worked up in the above-described manner to produce a product that was explosive upon heating. Brown gas is evolved upon acidification and NO is detected by chemiluminescence. Yield: 3.1 g; mp detonates at 182° C.; UV-vis $\lambda_{max}$=264 nm in 10 mM NaOH.

EXAMPLE 14

This Example describes the conversion of methylaminoacetonitrile to an NO-releasing imidate.

A solution of 3.8 g (0.035 moles) methylaminoacetonitrile hydrochloride was first converted to the free base with 25% sodium methoxide. The sodium chloride was filtered and the filtrate diluted with 50 mL of methanol. To this solution, 16 mL (0.07 moles) of 25% sodium methoxide was added, and the solution was degassed and pressurized with NO. Precipitate is noticeable within an hour but consumption of NO gas is sluggish. The white product obtained by filtration produces gas bubbles upon acidification. Yield: 0.856 g; UV-vis $\lambda_{max}$=262 nm in 10 mM NaOH.

EXAMPLE 15

This Example describes the conversion of propionitrile to an NO-releasing imidate.

A solution of 25 mL propionitrile and 12 mL (0.052 moles) sodium methoxide was degassed and pressurized to 2.7 atm (40 psi) of NO gas. Within 2 hours precipitate was observed and a white powder was obtained by filtration. Yield: 670 mg; UV-vis $\lambda_{max}$=262 nm in 10 mM NaOH.

EXAMPLE 16

This Example describes the conversion of butyronitrile to an NO-releasing imidate.

A solution of 50 mL diethyl ether, 1 mL methanol, and 25 mL butyronitrile was mixed with 10 mL (0.043 moles) of 25% sodium methoxide, degassed, and placed under 2.7 atm (40 psi) NO gas. A grayish powder was obtained by filtration. Yield: 1.07 g; UV-vis $\lambda_{max}$=262 nm in 10 mM NaOH.

EXAMPLE 17

This Example describes preparing the imidate first and then forming the diazeniumdiolated imidate in situ.

A solution of 5 mL (0.079 moles) chloroacetonitrile was allowed to react in 10 mL of a methanol/methoxide solution (0.043 moles methoxide) at room temperature for 35 minutes. The solution was degassed and placed under 2.04 atm (30 psi) NO gas. The tan colored precipitate was isolated 2 days later by filtration and dried for a yield of 2.35 grams. The material turns blue in a 2.0 M solution of HCl with effervescence and has a UV-vis $\lambda_{max}$=262 nm in water.

EXAMPLE 18

This Example describes preparing the bis-diazeniumdiolated amide directly from the diazeniumdiolated nitrile in situ.

This method precludes the formation of an imidate by avoiding the sodium methoxide/methanol method. Sodium hydroxide (1.73 g, 0.043 moles) was added to a stirred solution of 2.5 mL (0.0216 moles) of benzyl cyanide, 10 mL diethyl ether and 1 mL of water. The solution was degassed and pressurized to 2.7 atm (40 psi) of NO gas. The solution darkened as the reaction proceeded and a product precipitated overnight. The product was isolated by filtration and dried. There was no nitrile absorption in the IR spectrum. Yield: 726 mg; UV-vis $\lambda_{max}$=262 nm in 10 mM NaOH.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula (I);

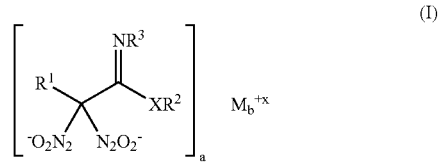

wherein

X is O or S;

R$^1$ is hydrogen, an unsubstituted or substituted C$_{1-12}$ straight chain alkyl, an unsubstituted or substituted C$_{3-12}$ branched chain alkyl, an unsubstituted or substituted C$_{3-12}$ straight chain alkenyl, an unsubstituted or substituted C$_{3-12}$ branched chain alkenyl, an unsubstituted or substituted alkoxy, halo, an unsubstituted or substituted benzyl, an unsubstituted or substituted phenyl, amino, an unsubstituted or substituted alkylamino, an unsubstituted or substituted arylamino, an unsubstituted or substituted dialkylamino, an unsubstituted or substituted diarylamino, an unsubstituted or substituted tolyl, xylyl, anisyl, mesityl, an unsubstituted or substituted alkylthio, an unsubstituted or substituted alkyloxy, an unsubstituted or substituted phenoxy, an unsubstituted or substituted benzyloxy, or nitro;

R$^2$ is an unsubstituted or substituted C$_{1-12}$ straight chain alkyl or an unsubstituted, substituted C$_{3-12}$ branched chain alkyl, or a phenyl;

R$^3$ is hydrogen, an unsubstituted or substituted C$_{1-12}$ straight chain alkyl, an unsubstituted or substituted C$_{3-12}$ branched chain alkyl, an unsubstituted or substituted C$_{3-12}$ straight chain alkenyl, an unsubstituted or substituted C$_{3-12}$ branched chain alkenyl, an unsubstituted or substituted C$_{3-8}$ cycloalkyl, benzyl or substituted benzyl, or phenyl or substituted phenyl; and M$^{+x}$ is a pharmaceutically acceptable cation, x is the valence of the cation, and a and b are the smallest integers that result in a neutral compound, wherein the compound is bound to a polymer.

2. The compound of claim 1, wherein the polymer is a biopolymer.

3. The compound of claim 1, wherein $R^1$ is substituted with at least one nitric oxide-releasing functional group.

4. The compound of claim 1, wherein $R^1$ is unsubstituted or substituted benzyl or unsubstituted or substituted phenyl.

5. The compound of claim 1, wherein $R^3$ is hydrogen.

6. The compound of claim 1, wherein each of $R^1$, $R^2$, and $R^3$ is optionally substituted each with 1 to 3 substituents independently selected from the group consisting of alkyl, aryl, alkoxy, aryloxy, acyloxy, benzyl, benzyloxy, acetyl, carboxyl, carboxyalkyl, carboxyalkylamido, carboxydialkylamido, carboxamido, alkylcarbonyl, arylamino, diarylamino, nitrile, tolyl, xylyl, mesityl, anisyl, pyrrolidinyl, formyl, dioxane, alkylthiol, heteroaryl, such as pyran, pyrrole, furan, thiophene, thiazole, pyrazole, pyridine, or pyrimidine, phenylcarbonyl, benzylcarbonyl, nitrophenyl, trialkylsilyl, nitro, sulfonyl, nitrobenzyl, trialkylammonium, tetrahydrofuranyl, tetrahydropyranyl, piperdinyl, morpholinyl, halo, cyano, hydroxy, thiol, cycloalkyl, amino, alkylamino, and dialkylamino.

7. A pharmaceutical composition comprising at least one compound of claim 1 and a pharmaceutically acceptable carrier.

8. A compound of the formula (I):

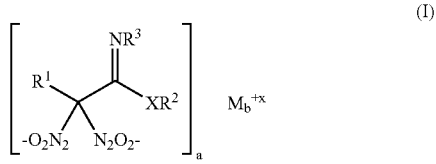

wherein

X is O or S;

$R^1$ is hydrogen, an unsubstituted or substituted $C^{1-12}$ straight chain alkyl, an unsubstituted or substituted $C^{3-12}$ branched chain alkyl, an unsubstituted or substituted $C_{3-12}$ straight chain alkenyl, an unsubstituted or substituted $C_{3-12}$ branched chain alkenyl, an unsubstituted or substituted alkoxy, halo, an unsubstituted or substituted benzyl, an unsubstituted or substituted phenyl, amino, an unsubstituted or substituted alkylamino, an unsubstituted or substituted arylamino, an unsubstituted or substituted dialkylamino, an unsubstituted or substituted diarylamino, an unsubstituted or substituted tolyl, xylyl, anisyl, mesityl, an unsubstituted or substituted alkylthio, an unsubstituted or substituted alkyloxy, an unsubstituted or substituted phenoxy, an unsubstituted or substituted benzyloxy, or nitro;

$R^2$ is an unsubstituted or substituted $C_{1-12}$ straight chain alkyl or an unsubstituted, substituted $C_{3-12}$ branched chain alkyl, or a phenyl;

$R^3$ is hydrogen, an unsubstituted or substituted $C_{1-12}$ straight chain alkyl, an unsubstituted or substituted $C_{1-12}$ branched chain alkyl, an unsubstituted or substituted $C_{3-12}$ straight chain alkenyl, an unsubstituted or substituted $C_{3-12}$ branched chain alkenyl, an unsubstituted or substituted $C_{3-8}$ cycloalkyl, benzyl or substituted benzyl, or phenyl or substituted phenyl; and $M^{+x}$ is a pharmaceutically acceptable cation, x is the valence of the cation, and a and b are the smallest integers that result in a neutral compound, wherein the compound is bound to a substrate.

9. The compound of claim 8, wherein $R^1$ is substituted with at least one nitric oxide-releasing functional group.

10. The compound of claim 8, wherein $R^1$ is unsubstituted or substituted benzyl or unsubstituted or substituted phenyl.

11. The compound of claim 8, wherein $R^3$ is hydrogen.

12. The compound of claim 8, wherein each of $R^1$, $R^2$, and $R^3$ is optionally substituted each with 1 to 3 substituents independently selected from the group consisting of alkyl, aryl, alkoxy, aryloxy, acyloxy, benzyl, benzyloxy, acetyl, carboxyl, carboxyalkyl, carboxyalkylamido, carboxydialkylamido, carboxamido, alkylcarbonyl, arylamino, diarylamino, nitrile, tolyl, xylyl, mesityl, anisyl, pyrrolidinyl, formyl, dioxane, alkylthiol, heteroaryl, such as pyran, pyrrole, furan, thiophene, thiazole, pyrazole, pyridine, or pyrimidine, phenylcarbonyl, benzylcarbonyl, nitrophenyl, trialkylsilyl, nitro, sulfonyl, nitrobenzyl, trialkylammonium, tetrahydrofuranyl, tetrahydropyranyl, piperdinyl, morpholinyl, halo, cyano, hydroxy, thiol, cycloalkyl, amino, alkylamino, and dialkylamino.

13. The compound of claim 1, wherein the polymer comprises polyolefin, polyether, polysaccharide, polyester, polyamide, polyurethane, or polyethylenimine.

14. The compound of claim 13, wherein the polymer comprises polystyrene, polypropylene, polyethylene, polytetrafluorethylene, polyvinyl chloride, polyvinylidene difluoride, polyethylene glycol, dextran, chitosan, poly(lactide/glycolide), or nylon.

15. The compound of claim 2, wherein the biopolymer comprises a peptide, a polypeptide, an enzyme, a protein, an oligonucleotide, an antibody, or a nucleic acid.

16. The compound of claim 8, wherein the substrate comprises metal, glass, ceramic, plastic, or rubber.

17. The compound of claim 8, wherein the substrate is a medical device.

18. The compound of claim 17, wherein the medical device is a blood oxygenator, a blood pump, a blood storage bag, a blood collection tube, a blood filter, tubing, a vascular graft, a stent, a pacemaker lead, a heart valve, a catheter, a guide wire, an amniocentesis or biopsy needle, a cannula, a drainage tube, a shunt, a sensor, a transducer, a probe, an artificial joint, or an artificial heart.

* * * * *